United States Patent
Schütze et al.

[11] Patent Number: 5,998,129
[45] Date of Patent: Dec. 7, 1999

[54] METHOD AND DEVICE FOR THE CONTACTLESS LASER-ASSISTED MICROINJECTION, SORTING AND PRODUCTION OF BIOLOGICAL OBJECTS GENERATED IN A PLANAR MANNER

[75] Inventors: Karin Schütze; Raimund Schütze, both of Wolfratshausen, Germany

[73] Assignee: P.A.L.M. GmbH, Wolfratshausen, Germany

[21] Appl. No.: 09/125,083

[22] PCT Filed: Jan. 31, 1997

[86] PCT No.: PCT/EP97/00429

§ 371 Date: Aug. 5, 1998

§ 102(e) Date: Aug. 5, 1998

[87] PCT Pub. No.: WO97/29355

PCT Pub. Date: Aug. 14, 1997

[30] Foreign Application Priority Data

Feb. 5, 1996 [DE] Germany .......................... 196 03 996
Apr. 23, 1996 [DE] Germany .......................... 196 16 216

[51] Int. Cl.[6] ................. C12Q 1/00; C12Q 1/08
[52] U.S. Cl. ............. 435/4; 435/40.5; 435/283.1; 435/40.52; 435/9.68; 435/973
[58] Field of Search ........................ 435/4, 40.5, 283.1, 435/40.52, 968, 973

[56] References Cited

U.S. PATENT DOCUMENTS

| | | |
|---|---|---|
| 4,243,887 | 1/1981 | Hillenkamp et al. .................. 435/4 |
| 4,624,915 | 11/1986 | Schindler et al. .................. 435/4 |
| 4,629,687 | 12/1986 | Schindler et al. .................. 435/4 |

FOREIGN PATENT DOCUMENTS

| | | |
|---|---|---|
| 9700429 | 1/1997 | European Pat. Off. . |
| 25 05 774 | 8/1976 | Germany . |
| 26 45 324 | 4/1977 | Germany . |
| 26 50 166 | 6/1977 | Germany . |
| 28 19 711 | 2/1984 | Germany . |
| 35 09 273 | 9/1986 | Germany . |
| 26 49 912 | 7/1987 | Germany . |
| 40 17 804 | 3/1991 | Germany . |
| 42 26 694 | 2/1993 | Germany . |
| 41 38 468 | 6/1993 | Germany . |
| 43 00 698 | 7/1994 | Germany . |
| 34 26 473 | 2/1996 | Germany . |
| 2 227 601 | 8/1990 | United Kingdom . |

OTHER PUBLICATIONS

Ponelies, N. et al.; Laser micromanipulators for biotechnology and genome research, In *Journal of Biotechnology* 35, 1994, pp. 109–120.

Patent Abstracts of Japan, 6–225750, Nov. 15, 1994, vol. 18, No. 597.

Patent Abstracts of Japan, 5–76342, Jul. 23, 1993, vol. 17, No. 394.

Patent Abstracts of Japan, 4–356183, Apr. 28, 1993, vol. 17, No. 216.

Patent Abstracts of Japan, 4–299976, Mar. 9, 1993, vol. 17, No. 113.

Patent Abstracts of Japan, 3–15380, Mar. 29, 1991, vol. 15, No. 132.

Patent Abstracts of Japan, 2–76574, Jun. 8, 1990, vol. 14, No. 265.

Patent Abstracts of Japan, 62–259578, Apr. 30, 1988, vol. 12, No. 143.

*Primary Examiner*—Louise N. Leary
*Attorney, Agent, or Firm*—Wenderoth, Lind & Ponack, L.L.P.

[57] ABSTRACT

The invention discloses a process for sorting and harvesting biological objects on a planar carrier (2). On a planar carrier (2) an object field or the object itself, located on the carrier (2), is cut out with a laser beam (6) and transferred by means of a laser-induced transport process to a collector substrate (5) which is disposed directly above or below the carrier. During the cutting-out process, either the laser beam (6) moves in a closed curve about the object or the object itself is cut directly out of the carrier (2) in a computerized manner. This method enables individually selected objects to be spatially separated and sorted from a very large number of objects. The method can also be used to separate specific cells from tissue sections.

15 Claims, 3 Drawing Sheets

METHOD AND DEVICE FOR THE CONTACTLESS LASER-ASSISTED MICROINJECTION, SORTING AND PRODUCTION OF BIOLOGICAL OBJECTS GENERATED IN A PLANAR MANNER

The invention concerns a process and apparatus for micro injection, sorting and harvesting of single biological objects. The objects are disposed side by side on a fixed planar carrier. This process is suitable for the micro injection of specific substances into individual biological objects, for example cells, and subsequently to sort them. Further with this process single objects can be spacially separated from a very great number of objects (e.g. $10^5$ to $10^9$) and singled out. The separation of heaped up cells/cell clumps as a unit is also possible. Also the process can be used for the separation of specific cells from a tissue sample. A precondition for this sorting process is the prior recognition and selection of the objects concerned on the basis of specific (qualities (e.g. by color, fluorescence marking or by radioactive marking). Within tile term "biological objects" in the context of the present application is meant mainly live or trapped biological cells or parts of cells.

For injection of material into livinig cells usuially micro capillary tubes were used that were usually controlled by usually a pneumatic or hydraulically moveable micro manipulator. The desired substances are injected into the individual cells under great mechanical stress. The manufacture of sterile micro capillary tubes is tine consuming and expensive.

Tsukakosli et al. (1974) and Tao et al. (1987) used a focused laser beam to drill small self healing holes without mechanical contact in a cell membrane. The short opening time is sufficient for the material that is dissolved in the surrounding fluid to penetrate the cell. A larger efficiency in laser micro injection of genetic material was achieved when the laser blasts the hole directly into the cell.

The problem with this method is that for a precise laser micro injection in the submicron region the target objects have to be approached with an accuracy of the order of nanometers in the lateral, that is in the X/Y direction, and also in the vertical, that is in the Z direction. For an automated micro injection the relevant target cells have to be recognized via an image recognition process, then positioned in the line of fire of the laser and most importantly then exactly focused in the Z direction.

A further problem is to isolate or to prepare the successfully injected cells from the other cells for further tests.

For the separation of single biological objects there exist optical methods, such as the optical tweezer in which the object moves in an aqueous solution (K. Schütze, A. Clement-Sengwald, Nature 667 (vol. 368) 1994). On account of the very small transfer of force this method is limited to objects that are able to move freely in the solution. As the sorted and unsorted objects are in the same solution a separate cultivation is only achievable with extra expenditure of effort. For a separate cultivation of cells they have to be separated or sucked apart by another method, for example, with micro capillary tubes. Adherently growing cells or trapped cells on a dissected sample can be separated with a fine needles that are moved by means of a micro manipulator. In this situation the cells are contacted directly and thereby can be mechanically stressed. In addition there is the danger of contamination by undesired cell material. Both methods are comparatively time consuming such that they are not suitable for the manipulation of a large number of objects.

For the separation of single cells from a large number (>$10^6$) dispersed in a fluid there are commercially available devices for separating and sorting biological objects. While in the fluorescence activated cell sorter (FACS) electro static principles for the spacial separation are used the magnetic activated cell sorter (MACS) operates with magnetic forces. In these systems the cells are however, not disposed side by side on a planar carrier. In addition both of these methods have the disadvantage that many of objects can only be separated to a limited extent (FACS) or even not be separated from each other at all (MACS).

The above described methods cannot release single cells from a cell plaque/cluster such as a tissue or from a histological tissue preparation.

An apparatus is known from JP-A-05 076342 for catching and collecting microscopic objects such as cells. In this arrangement the object of interest is captured by two continuous lasers disposed opposite each other and is held in place. Then it is guided to a collection apparatus by a third continuous laser along its beam. From the article "Cell surgery by laser micro-dissection: a preparative method" *in Journal of Microscopy*, Vol. 107 (1976) an apparatus is known which used a quasi-continuous $N_2$-Laser for microdissection, and a microscope is used for the subsequent observation of the selected object.

Further there are processes known under the name of "ablative photo decomposition" in which a directed removal of polymer material is achieved using pulsed UV-lasers particularly Eczema lasers. This process can in the wider sense be seen as an etching process. A similar process which however uses a continuous UV-laser is described in U.S. Pat. No. 5,211,805. This process is stated to be suitable for the industrial processing of technical polymers and for the biomedical treatment of biological tissue. A sorting principle is used that involves the destruction of undesirable biological objects on a carrier by means of a laser radiation of a high dosage, while the selected (desired) object remains behind (U.S. Pat. No. 4,624,915). This procedure is relatively troublesome for selecting a single object from a large population.

The object of the invention is among other things, is a directed manner, to load biological objects with a selective substance by means of contactless laser micro-injection and subsequently to sort the successfully injected objects. The biological objects can be distributed side by side on a fixed planar carrier, for example a polymer carrier foil. In this connection the selection process should be conductahle as quickly as possible (<10s) and without contact, e.g. in a separate sterile chamber. In addition the procedure must be very reliable and therefore be able to be automated in a simple way. At the same time the biological objects should have a high survival rate and as a rule remain unchanged. The objects should not be damaged or injured by the micro injection procedure and the separation process.

The task of micro injection is conducted in accordance with the invention in an automated manner in that an object field on the cover glass or a carrier foil is removed by a meander shaped scan with the motorized computer controlled microscope carrier. In this way the single target cell (target object) is selected by means of an image analysis process using color or pattern recognition and by means of X/Y displacement is brought into the region of the laser shot. Subsequently the cell or the desired cell structure is brought into focus (in the Z direction), an with a directed laser shot the cell is micro perforated. The movement of the object in the X/Y direction can either be set via the axis of the microscope table and the Z direction by a third axis of the microscope table or can be set via the focus adjustment of the objective on the microscope itself by computer control. Alternatively an adjustment onto the target object can be achieved even with a fixed microscope table by means of a 3-dimensional computer controlled laser focus movement. In order to sort out the successfully micro injected cells subsequently from the remaining cell lawn the selection process that will now be described is used.

The task of the selection and separation is achieved in accordance with the invention in that an object field of the carrier foil on which the selected biological object or the histological dissection is disposed, is cut out with a laser beam and transferred by a laser induced transport process to a collecting substrate which is directly above or below the carrier foil. The solution in accordance with the invention is that the biological object first is either identified visually with the eye, or by means of a color or pattern recognition of an image analyzing process and subsequently cut out in a surrounding that suits the sample, for example also in a circle together with the carrier by a laser beam and subsequent to that flung out of the carrier foil and onto a collector disposed in the vicinity. It was observed that the separated out object field is always flung in the direction of the laser beam. A physical explanation for this laser induced transport process lies possibly in the photokinetic impulse that is transferred from the laser beam to the cut out object field and which is thereby responsible for the acceleration. The spacial separation of the biological object is attributable thus in this process to the cutting out of the desired object field together with the previously selected object and its conveyance to the collecting substrate that is disposed in the vicinity.

The cutting out of the object field can advantageously be achieved by providing that the laser beam is guided in a closed curve around the biological object that includes the object field by means of a relative movement of the laser beam and the carrier foil. Alternatively, the separation of the object field, by analogy to a stamping process can also be conducted whereby the cutting area including the object field is simultaneously exposed through a slit mask that is illuminated by the laser beam and projects onto the carrier foil.

As already mentioned the collector substrate should be in the immediate vicinity of the carrier foil so that the distances to be transported during the separation process are short. Good results were achieved with distances of 0.5 to 10 mm, preferably 1 to 3 mm.

The diameter of the object field with the selected object can, on account of the extraordinarily precise cutting process, be selected to be in the region of 10 micro meters to 20 micro meters.

For the cutting out preferably a UV laser is used, and at the same time the focus of the laser beam on the carrier foil is reproduced as an image thereon.

The carrier foil consists of a UV absorbing polymer foil with a thickness between 5 micro meters and 15 micro meters that's absorption behavior is matched to the wavelength of the UV laser or at least has an absorption maximum in the region of the laser wavelength. Polymer foils have proved to be particularly suitable that contain 5 weight % of an aromatic or partly aromatic polycondensate. The geometrical form of the collector substrate is relatively uncritical. Suitable, for example is a relatively thick foil or plate that is disposed at a distance of 0.5 to 10 mm above or below the carrier film and parallel thereto. The collector substrate can however be constructed in the form of a pot shaped holder. In particular micro centrifuge containers are recommended of the type that are used in molecular biology, for example, a micro titration plate with 90 to 500 wells.

In accordance with a special embodiment a plate or foil is provided with an adhesive coating. By means of such an adhesive coating the object field that has been propelled can be retained on the collector substrate.

For the purpose of recognition and selection of the desired biological object on the carrier foil the method of fluorescent spectroscopy can preferably be employed.

Alternatively the biological object can be recognized and subsequently selected with the help of known histochemical color reactions or morphologically perceptible changes, either visually or by an image analysis procedure on a computer.

In accordance with a further development the biological objects are coated with a fluid nutrient or buffer medium that is transparent to the laser radiation. In these circumstances the selected object fields can in accordance with the invention be cut out and released.

The separation process in accordance with the invention is carried out to advantage in a closed system. To this end the carrier foil with the objects to be sorted and also the collector substrate are housed in a closed container that has a UV transparent window for the laser beam.

In what now follows, the invention will be explained in more detail with reference to the drawings and embodiments.

BRIEF DESCRIPTION OF DRAWINGS

The drawings show:

FIG. 1 shows for example a population of bacteria 1 that is distributed in a planar manner on a 5 micrometer thick foil of polyacrylate 2 (carrier foil). For the sorting process the carrier foil 2 is placed in a displaceable table 3 and held mechanically. This table in accordance with FIG. 2 is the objective table in an inverting microscope 4 and can, for example, be positioned by means of computer controlled stepping motors in X/Y directions (in a horizontal plane). In the displaceable table 3 and opposite the carrier foil 2 at a distance of 1.8 mm there is retained a plate shaped collector substrate 5, upon movement of the displaceable table 3 therefore the carrier foil 2 and the collector substrate 5 move together at right angles to the path of the radiation (Z direction) in the microscope. The moveable table 3 with the carrier foil 2 and the biological objects 1 that are disposed thereon and the collector substrate 5 are surrounded by a closed housing that is provided with a window transparent to ultraviolet light for the laser beam (not shown). In this way the process can be carried out in a hermetically sealed system.

Figure 1:
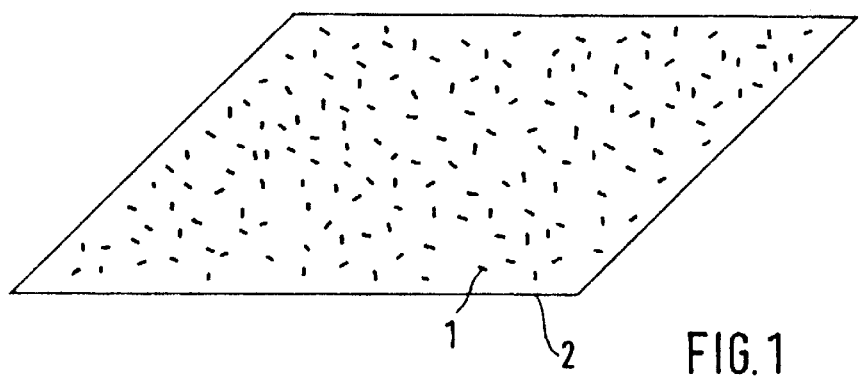
FIG. 1. schematically a carrier foil with adhered bacteria.
Figure 2:
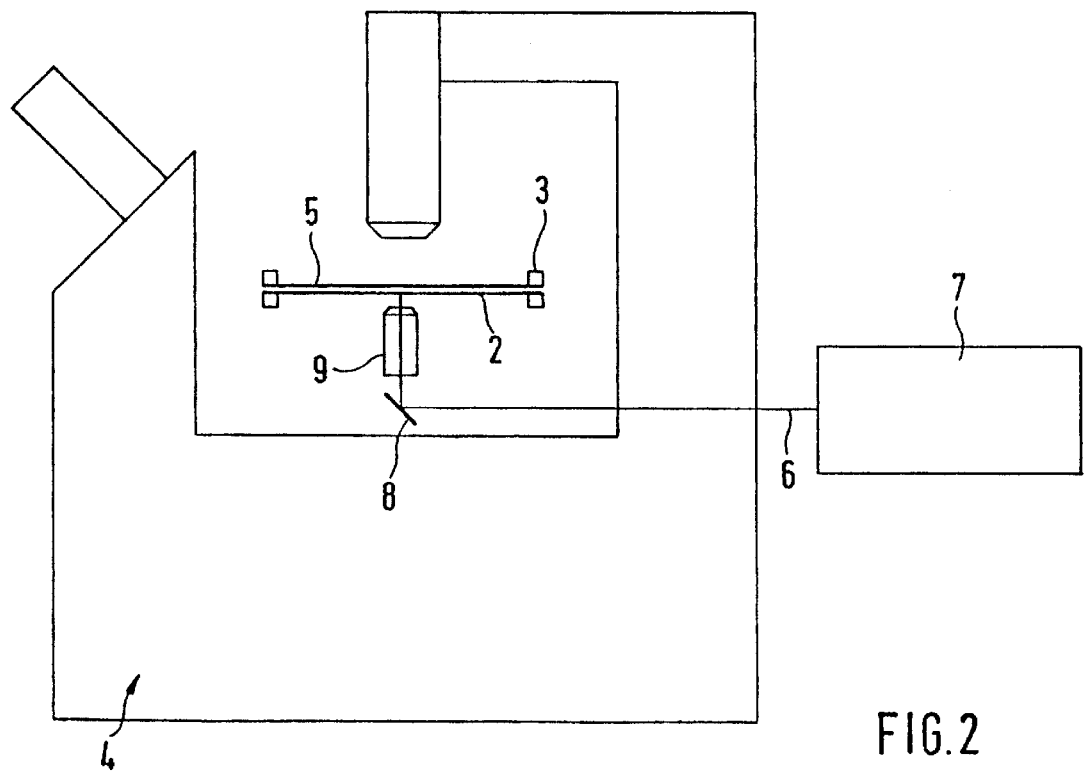
FIG. 2. the fundamental construction of apparatus for carrying out the process according to the invention.

As the carrier film for the biological objects is an ultra violet absorbing polyinerfilm of thickness 5 micro meters to 15 micro meters that contains at least 5 weight percent of an aronmatic or partly aromatic polycondensate, for example polycarbonate, polyurethane, polyacrylate, co-polyester, polyester carbonate or a blend of these polycondensates and other thermo-plastic materials. Other types of foil are conceivable within this context.

For the spacial separation, for example of single bacteria from the recovered population a UV-laser beam 6 of wavelength 337 nano meters of a pulsed $N^2$-laser 7 is used. The laser 7 delivers approximately 300 micro joules of radiation energy with a maximum pulse frequency of 20 Hz. Also suitable are other pulsed or continually operating lasers for example an Eczema laser with a wave length of 193, 248 or 308 nm or a frequency quadrupled Nd;YAG-laser with a wave length of 266 nm or a frequency doubled AR-Ion laser with a wave length of 244 nm or 257 nm. The laser beam 6 is projected onto the carrier foil 2 in a dot shape via a dielectric beam splitter 8 and a reducing microscope objective 9 (reduction 63×, aperture NA=0.9 or also other objectives). This dot has a diameter of at least 1 micrometer.

A circular or closed cutting line with a diameter of, for example, 10 micrometers is generated around these selected bacteria by a corresponding movement of the moveable table 3 in the horizontal plane. The area defined by the cutting line is in this case the object area. The laser beam remains stationary during the following described cutting process.

In the experiment the relative speed of movement of the laser beam to cut out a closed area was 5 micro meters per second. A sharp edged narrow bounded cutting line was generated and as the laser beam returns to the starting point of the cutting line a separation of the cut out area occurred. The area was propelled from the carrier foil 2 onto the adhesive coated collector substrate 5 by a laser induced transport physical process of which has not yet been explained in detail. There it remained captured. Another possibility is to use as the collector substrate a conventional micro titration plate with, for example 96 wells. By "wells" it is understood in the field of pharmaceutical research, to mean the cut outs or round depressions in the micro titration plate for receiving samples for testing and with a diameter of about 4 mm and a depth of about 6 mm.

Figure 3:
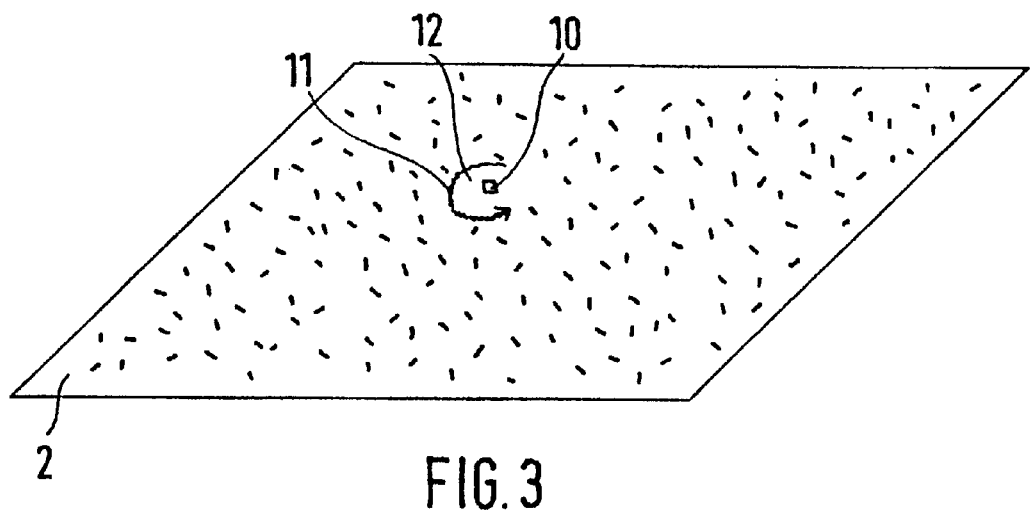
FIGS. 3/4. the underlying sorting principle.

The sorting process will be explained again with reference to FIGS. 3 and 4. FIG. 3 shows a bacteria 10 to be separated on a carrier foil 2. On account of the circular movement of the moveable table 3 a cutting line 11 of width of about 5 to 7 micro meters has already been drawn by a fixed position laser beam 6 in a cutting process. The width of the cut depends on the absorption properties of the foil. In this area the foil material is completely removed.

Figure 4:
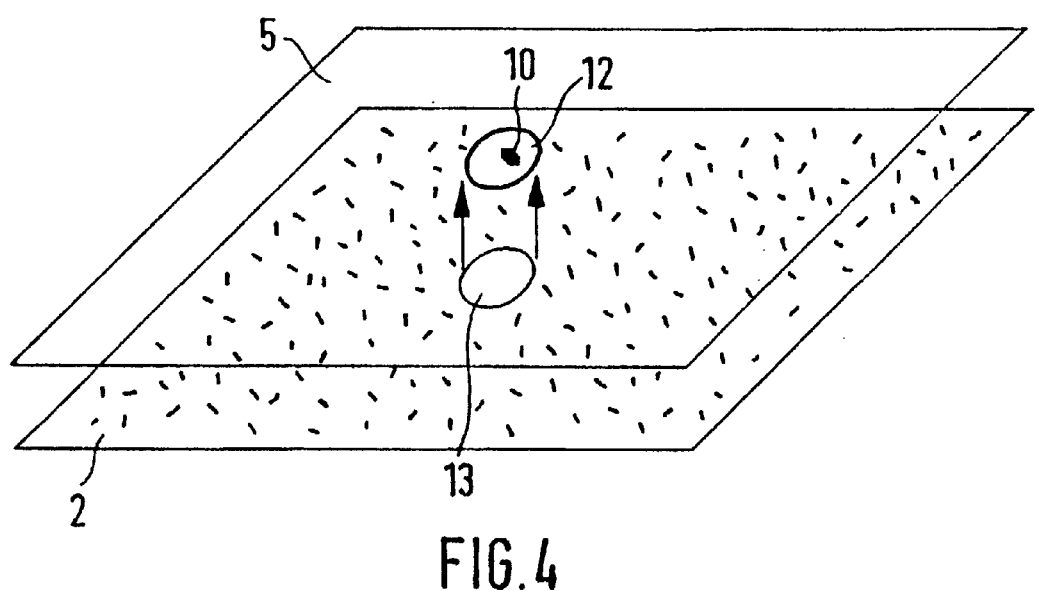

Immediately after the cutting line 11 has completed a closed circle the separated piece of foil (object field) 12 with the bacteria 10 on it is propelled in the direction of the laser beam and as shown in FIG. 4 catapulted onto the adhesive tape 5 (the collector substrate). A circular hole 13 remains in the carrier foil 2.

In place of a moveable table a stationary object table can be used and the laser beam can be made to draw a circle around the selected bacteria by a suitable optical deflection element disposed in the laser beam.

A prerequisite for the laser separation is that the object field to be removed from the carrier foil be previously recognized and selected. A method that is frequently used in pharmacological research for the recognition and selection of particular cell structures is fluorescent spectroscopy. For this purpose a commercially available fluorescence microscope is used. This presupposes that the cells or bacteria for the intended selection generate a significant fluorescence signal that can be used as the differentiating criterion. With the help of a scanning program equipped with a search algorithm the moveable table 3 can be so controlled that automatically and in turn the areas with selected bacteria can be positioned as object fields centrally in the field of view of the fluorescence microscope and subsequently cut out.

For the recognition of biological objects in sections of tissue the known histological color reactions or morphological changes that are observable under the microscope can be used.

The carrier foil 2 can also be coated with a laser radiation transparent nutrient or buffer solution, for example a PBS buffer solution.

Figure 6:
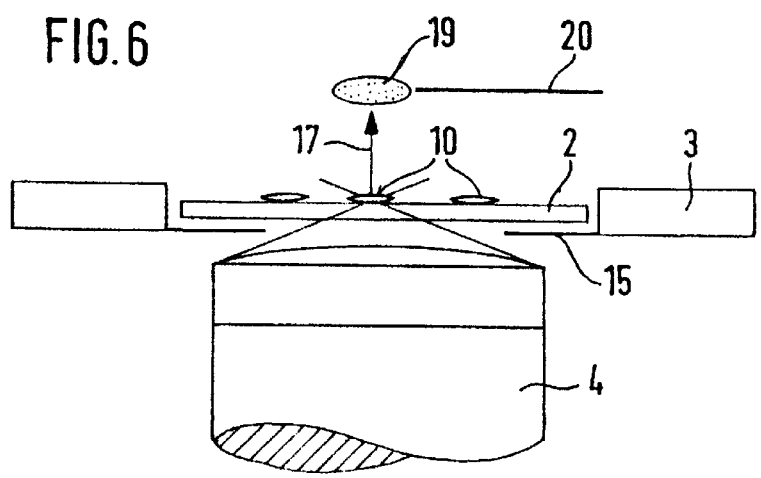
Figure 7:
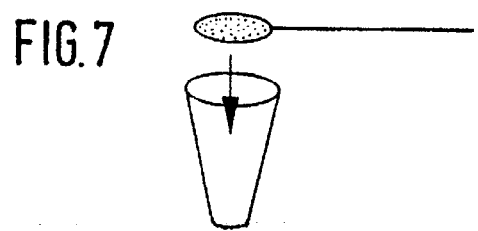
FIG. 7. the deposition of the object in a receptacle.

In accordance with a further development of the process, the object of the invention can be achieved by using the radiation pressure of the laser beam to catapult the desired particle or biological object itself directly from the upper surface of the fixed planar carrier (object carrier or petri dish) and to catch it in a suitable container, i.e. the separation of the biological object is thus possible, with or without, the simultaneous release or cutting out of the area of the carrier foil that is supporting the object. This occurs in accordance with the further development in the following manner; that will be described with reference to the accompanying FIGS. 5 to 7.

Figure 5:
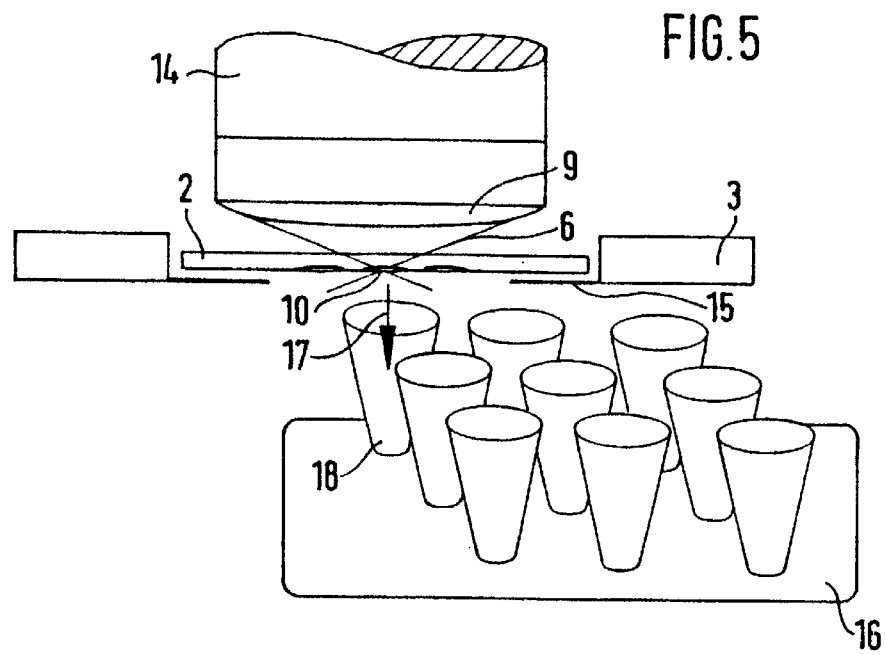
FIGS. 5/6 the construction of the upright/upside down microscope.

When using an upright microscope 14 in accordance with FIG. 5 a suitable object carrier 2 (thickness approximately 170 micro meters) is placed upside-down on the support 15 of a microscope table 3 especially designed for laser micro manipulation, i.e. the biological object 10 is on the under side of the object carrier 2. The object can for example be a histological tissue section of only a few micro meters thick or adhering chromosome or DNA preparation.

The microscope table 3 is equipped for a displacement in 2 axes (for X/Y movement) or 3 axes (for X/Y/Z movement) and is provided with a support 15 for, for example, the object carrier 2 or petri dishes. The table 3 is thus motorized by means of a suitable drive that can be moved under computer control in a known way, for example by a computer mouse (or joystick). The hybrid stepping motors of the axis drives work with a high precision. The smallest step is 20 nm the maximum traveling distance of the microscope table 3 can be up to several cm, for example 10 cm. The precision with which stored points can be found again is less than 400 nm. Speeds can be chosen for movement of the microscope table from a few nm to several mm per second. By means of a so-called "framegrabber" actual microscope pictures, that are taken via a video camera, are shown on a monitor anti can be graphically overlaid with computer functions, for example command functions, control functions, test points etc. (Video-overlay).

For the laser micro manipulation only thin object carriers (about 170 micro meters thick) or petri dishes with thin (approximately 25 micro meters) gas permeable foil (so-called "petri-perm" dishes) are suitable. As laser micro manipulation in the nano meter region sets a very high requirement on a precise holding and transport of the samples, the support 15 has been especially configured. With a thin object carrier 2 there is the danger, for example when an oil emersion objective is used, of slight bending and thereby a good focus cannot be achieved. In order to prevent this the object carrier 2 must be supported on at least three sides of the holder. The two narrow sides of the object carrier 2 each can be held tightly with a spring clip. A further necessity peculiar to the laser microscopy is the exact adjustment of the sample holder (object carrier 2 or sample holder 15). It must be provided that the sample is always the same distance from the tip of the objective 9 over the whole range of movement of the carrier (approximately 5–10 cm).

First, suitable biological objects 10 are selected optically with a lower magnification. As soon as all objects of interest are stored in the computer a higher magnification objective is selected. The displacement of the beam due to the change of objective (chromatic aberration) is compensated for by a correction function acting on the stored values that is automatically applied to all stored points.

The computer then drives to the first object 10. A microscope image that is viewed by a video camera is displayed on the computer monitor, which is not shown in the figures. A marker on the monitor shows the position of the focus of the laser beam. The microscope slide is moved either by hand (controlled by a mouse or joystick), or travels automatically under the control of a computer program in accordance with a predetermined pattern in essentially circular or a spiral shape around the chosen object 10. The marker on the monitor can be regarded as a pointer with which the outline of the desired biological object is drawn. If at the same time the laser, with a pulse frequency of around 15 to 20 Hz, fires, all material that is in the line of fire in the region of the "marker" is removed or destroyed. The extremely focused laser beam "draws" a fine line of approximately 500 nm width around the desired object 10 and separates it thereby from its surroundings. In the case of cells in the histological section a desired cell can be released from the plaque/cluster by means of this procedure and loosens from the substratum in the shape of the object field given by the cutting line. By means of the above mentioned spiral shaped circulation around the chosen target cell the region around the cell that is left free can be enlarged.

The laser used in the procedure described is for example a pulsed compact nitrogen laser with a high quality beam (wave length: 337 nm, pulse length 3 n sec, pulse frequency: from 10 to 30 Hz). Other lasers are also envisaged, as long as the wave length of laser light used does not negatively influence the biological material. The laser beam itself, i.e. its source remains preferably stationary. However, the laser can also be moved in the X/Y direction with a radius of several micrometers relative to the plane of the object, i.e. in the final analysis it is only important that the laser beam and the plane of the object (the microscope table) be moved relative to one another.

The object that has been isolated in this manner can then, faster and safer than in the state of the art (for example with a needle), be automatically catapulted into a test vessel (trajectory 17) and most importantly without any contact, i.e. if necessary also completely sterile, with a further aimed laser shot.

To this end it is necessary that a second sample support 16 (for example to retain a collector vessel 18 or a microtitration plate), driven by two motorized and computer controlled axes, is moved in such a way beneath the first support 15, and the object 10 that has been isolated by the laser is exactly positioned above the collecting vessel 18. Here is accordingly a high precision of the motor movement a requirement for a clean collection of the desired object. A single aimed laser shot (possibly defocused) catapults the selected biological object 10 and/or the cell in the direction of the beam (trajectory 17) into the collecting vessel 18. Afterwards a new object can be cut out and the entire process repeated.

To accelerate the collection procedure all of the desired objects can first be released by the laser. Afterwards the collection vessel can be moved into position beneath the microscope table. The microscope slide then moves to revisit each of the stored laser micro dissected objects. Each shot of the laser then catapults a subsequent one of the objects into respective fresh (new) receiving vessels 18, FIG. 5, that coordinate with the movement of the microscope slide 3. Several objects could also be collected in one container.

With an upside down microscope (FIG. 6) a sticky plate adhesive foil, agar coated carrier etc. can be used, which is moved only a few micrometers directly above the object that has been cut out to catch the catapulted away object. This can, for example be a sticky member that is then thrown by means of robot arm 20 into a suitable container, FIG. 7. The robot arm 20 then picks up a new sticky member (see FIG. 6).

The advantage of the laser induced separation process of cells is the selective, and at the same time rapid, manipulation of single cells in comparison with the prior art. On account of the simple principle the procedure is very robust and easy to use and thereby suitable for the computerized automatic separation of a large number of biological objects. An important advantage considering safety aspects is that the separation process can be conducted in a hermetically sealed system so that the environment can be protected from pathogenic cells. Also the cells are protected from contamination from the environment.

The process is suitable mainly in the sub-fields of biotechnology, molecular biology and pathology where specific cell types have to be refined. For example transfused cells can be identified with the green fluorescent protein (GFP) as reportergen. Marshall et al. (Neuron, Vol. 14, 211–215 (1995)) uses for example the GFP method to assess the expression of ion channels. In accordance with a further application, for example, glea cells can be separated from brain tissue samples for neurological experiments. For this, fluorescent marked antibodies are used to identify the cells. For diagnosis tumor cells can be isolated from tissue samples that for example, show morphological changes. In this case the tissue slice is placed on the carrier foil. The cell to be isolated is then cut from the tissue and the foil substrate separated so that the cell possibly with the substrate material is transferred to a support. The cells are then subsequently histologically analyzed. In addition bacteria with specific properties, for example that produce citric acid can be tested for their efficiency by means of suitable pH sensitive colored rings of a suitable indicator and subsequently sorted.

We claim:

1. A process for sorting and harvesting of biological objects on a planar carrier on which selected biological objects are present together with other biological objects, the process comprising:

separating the selected biological object is separated from the surrounding other biological material by a laser beam such that the selected biological object is freed from its surroundings; and subsequently catapulting freed object on the carrier away from the carrier by a further laser shot to a collection device.

2. The process according to claim 1, further comprising: cutting out, by means of a laser beam, an object field of a carrier foil on which the selected biological object is disposed and transferring the object field by a laser induced transport process onto a collecting substrate that is directly above or below the carrier foil.

3. The process according to claim 2, characterized in that the laser beam is guided in a closed curve around the biological object that includes the object field.

4. The process according to claim 2, characterized in that the cut area that includes the object field is simultaneously exposed through a slit mask which is illuminated by the laser beam, and imaged on the carrier foil.

5. The process according to claim 2, characterized in that the object field with the biological object disposed thereon is transported after the cutting out thereof a distance of 0.5 to 10 mm.

6. The process according to claim 2, characterized in that the object field is cut out with a diameter of at least 5 micro meters.

7. The process according to claim 2, characterized in that a UV laser is used to cut out the object field.

8. The process according to claim 2, characterized in that a UV light absorbing polymer film with a thickness of 5 micro meters to 15 micro meters is used as the carrier foil for the biological object.

9. The process according to claim 8, characterized in that the polymer contains at least 5% by weight of an aromatic or part-aromatic polycondensate.

10. The process according to claim 2, characterized in that a foil with an adhesive upper surface is used as the collecting substrate.

11. The process according to claim 2, characterized in that a micro titration plate with 90 to 500 wells is used as the collecting substrate for the reception of samples.

12. The process according to claim 1, characterized in that the biological objects are recognized with the help of fluorescence spectroscopy and are subsequently selected.

13. The process according to claim 1, characterized in that the biological objects are dissected tissue and are recognized with the help of histochemical color reaction or a morphological visible change and are subsequently selected.

14. The process according to claim 2, characterized in that the carrier foil with the biological object thereon is coated with a fluid nutrition or buffer medium that is transparent to laser radiation.

15. The process according to claim 2, characterized in that the carrier foil with the objects to be sorted and the collection substrate are housed in a closed container which has a UV transparent window for the laser beam.

* * * * *